United States Patent
Lia et al.

(10) Patent No.: US 11,234,586 B2
(45) Date of Patent: Feb. 1, 2022

(54) MEDICAL DEVICE ILLUMINATOR AND CHARGING SYSTEM

(71) Applicant: Welch Allyn, Inc., Skaneateles Falls, NY (US)

(72) Inventors: Raymond A. Lia, Auburn, NY (US); Robert A. Vivenzio, Auburn, NY (US); Miguel C. Mudge, Syracuse, NY (US); Jon R. Salvati, Skaneateles, NY (US); Jeffrey Chiodo, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 411 days.

(21) Appl. No.: 16/509,551

(22) Filed: Jul. 12, 2019

(65) Prior Publication Data
US 2019/0335988 A1 Nov. 7, 2019

Related U.S. Application Data

(60) Continuation of application No. 15/239,891, filed on Aug. 18, 2016, now Pat. No. 10,362,932, which is a division of application No. 14/189,674, filed on Feb. 25, 2014, now Pat. No. 9,445,712.

(51) Int. Cl.
| | | |
|---|---|---|
| A61B 1/303 | (2006.01) |
| A61B 1/06 | (2006.01) |
| A61B 1/00 | (2006.01) |
| A61B 1/31 | (2006.01) |
| A61B 1/32 | (2006.01) |
| F21L 4/08 | (2006.01) |
| F21V 23/04 | (2006.01) |
| F21V 31/00 | (2006.01) |
| F21V 33/00 | (2006.01) |
| A61B 1/07 | (2006.01) |
| F21Y 115/10 | (2016.01) |

(52) U.S. Cl.
CPC .......... *A61B 1/303* (2013.01); *A61B 1/00034* (2013.01); *A61B 1/00105* (2013.01); *A61B 1/06* (2013.01); *A61B 1/0661* (2013.01); *A61B 1/0676* (2013.01); *A61B 1/0684* (2013.01); *A61B 1/31* (2013.01); *A61B 1/32* (2013.01); *F21L 4/08* (2013.01); *F21L 4/085* (2013.01); *F21V 23/0414* (2013.01); *F21V 31/005* (2013.01); *F21V 33/0068* (2013.01); *A61B 1/07* (2013.01); *F21Y 2115/10* (2016.08)

(58) Field of Classification Search
CPC .............................. A61B 1/303; A61B 1/0034
See application file for complete search history.

(56) References Cited

U.S. PATENT DOCUMENTS 2,592,190 A * 4/1952 Rubens .................... A61B 1/32
600/223
3,698,387 A 10/1972 Moore et al.
(Continued)

*Primary Examiner* — Andrew Yang
(74) *Attorney, Agent, or Firm* — Barclay Damon LLP

(57) ABSTRACT

A portable medical illuminator is configured for attachment to a medical device wherein the illuminator includes an illuminator housing and a light source disposed in relation to the housing. A portable rechargeable power supply is connected to the light source, and an inductive charging coil is disposed within the illuminator housing to enable contactless charging of the contained portable power supply.

20 Claims, 16 Drawing Sheets

(56) References Cited

U.S. PATENT DOCUMENTS

| | | | | |
|---|---|---|---|---|
| 3,789,835 A | * | 2/1974 | Whitman | A61B 1/32 |
| | | | | 600/223 |
| 3,885,211 A | | 5/1975 | Gutai | F21L 4/08 |
| | | | | 200/60 |
| 4,067,323 A | * | 1/1978 | Troutner | A61B 1/32 |
| | | | | 362/109 |
| 4,623,217 A | | 11/1986 | Hallen | A61B 1/07 |
| | | | | 362/581 |
| 6,379,296 B1 | * | 4/2002 | Baggett | A61B 1/303 |
| | | | | 600/178 |
| 8,435,175 B2 | | 5/2013 | McMahon et al. | |
| 2008/0228038 A1 | | 9/2008 | McMahon | A61B 1/00105 |
| | | | | 600/223 |
| 2009/0097236 A1 | * | 4/2009 | Miller | A61B 1/32 |
| | | | | 362/119 |
| 2011/0234155 A1 | | 9/2011 | Chen | A61N 1/3787 |
| | | | | 320/108 |
| 2012/0209079 A1 | | 8/2012 | McMahon | A61B 1/00105 |
| | | | | 500/223 |
| 2013/0096539 A1 | | 4/2013 | Wood | H02J 7/02 |
| | | | | 606/1 |

\* cited by examiner

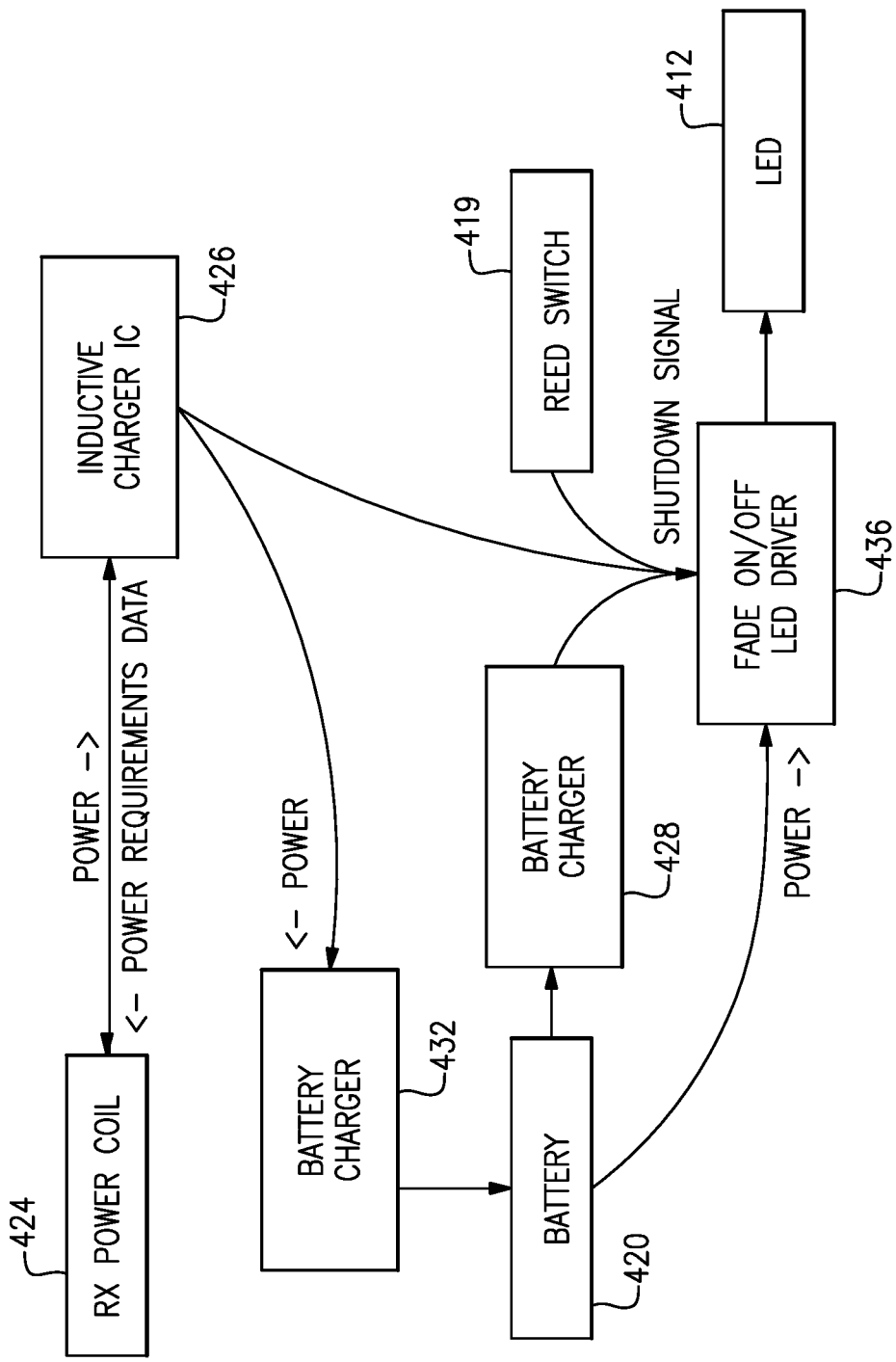

MEDICAL DEVICE ILLUMINATOR AND CHARGING SYSTEM

CROSS REFERENCE TO RELATED APPLICATION

This application is a continuation of U.S. Ser. No. 15/239,891, filed Aug. 18, 2016, and entitled: Medical Device Illuminator and Charging System, which is a divisional of U.S. Ser. No. 14/189,674, filed Feb. 25, 2014, and entitled: Medical Device Illuminator and Charging System, filed pursuant to relevant portions of 35 U.S.C. § 120. The entire contents of each application herein being incorporated by reference.

TECHNICAL FIELD

This application generally relates to the field of medical diagnostic devices and more specifically to a portable illuminator used in conjunction with a medical diagnostic instrument, the illuminator having a battery power source that can be inductively charged.

BACKGROUND

Various known medical devices, such as medical diagnostic instruments, can be equipped with dedicated or attachable illumination assembles to aid in the visualization of a target of interest. Examples of diagnostic instruments having dedicated illumination supplies include those described in U.S. Pat. No. 3,698,387, the entire contents of which are incorporated by reference herein. According to this patent, an otoscope is defined by a handle portion and an instrument head attached to an upper end of the handle portion. The handle portion has an interior appropriately sized to retain a set of batteries in stacked relation as well as a light source, such as an incandescent lamp, the latter being disposed in an upper portion of the handle portion. The output of the contained lamp is coupled to the proximal end of a bundle of optical fibers that extends as a circular ring at a distal end of an insertion portion of the instrument head. A speculum tip member is attached to the insertion portion in overlaying, releasable fashion so as to enable viewing of the target (i.e., outer ear or tympanic membrane) through an eyepiece that is provided at the proximal end of the instrument head. Additional details relating to the above instrument are provided in the above incorporated '387 patent. Later versions of these instruments have incorporated rechargeable batteries. In at least one such version, these batteries can be recharged without having to remove the batteries from the handle portion using a suitable adapter.

Referring to FIGS. 1(a) and 1(b), an example of a medical instrument assembly 200 that includes a releasably attachable illumination assembly is described in which a portable, battery powered reusable illuminator 230 is configured and sized for axial insertion within an enclosed receiving cavity 217 of a disposable vaginal speculum 204. The enclosed receiving cavity 217 is part of a downwardly extending handle portion 216 having a cross section which is adapted and sized to receive an axial portion of the illuminator 230. When properly positioned within the receiving cavity 217, the illuminator 230 is positioned such that a contained light source, such as a white LED, disposed at an upper end 238 of the illuminator housing 234 is coupled optically with the proximal end of an integrated light pipe (not shown) extending from the receiving cavity 217 and along an inner surface of a trough-shaped portion of a lower blade 214 of the vaginal speculum 204. When energized, light emitted by the LED is internally reflected through the light pipe and transmitted at a distal end and through the trough shaped portion of the lower blade 214 towards the target (i.e., cervix) of a female patient. The target can be viewed by the caregiver through a rear opening or aperture 221, which is defined between an upper blade 212 and the lower blade 214 of the speculum 204, the blades 212, 214 being made adjustably movable relative to one another to permit dilation of the cervix of the patient using an articulation mechanism. This latter mechanism includes a slide member 220 having a yoke 228 disposed at an upper end of the slide member 220. A curved section 225 extending from the center of the yoke 228 includes a set of spaced engagement teeth 226 that can be engaged by a lever portion 224, the latter extending from the proximal end of the upper blade 212 wherein the upper blade 212 is hingably connected to the lower blade 214 at respective sides of the yoke 228. The lever portion 224 and the yoke 228 are each configured to enable access to the interior of the speculum 204 through the rear opening 221 and in which the curved portion 225 extends upwardly and rearwardly through the lever portion 224 wherein the curved portion 225, and more specifically the engagement teeth 226, engage an interior surface of the lever portion 224 adjacent an extending bottom tab 227 thereof. The slide member 220 is further adjustable using a lower tongue 229 that engages features provided on the rear facing side of the handle portion 216, including a guide slot 223 having sets of external teeth 222 disposed along the length of the slot 223 on opposing sides.

Still referring to FIGS. 1(a) and 1(b), the illuminator 230 is enabled such that the contained LED is automatically energized upon axial insertion into the receiving cavity 217 and more specifically due to engagement between an external contact switch 248 on one lateral side of the illuminator housing 234 with corresponding features (not shown) that are provided within the walls of the receiving cavity 217 in combination with a spring loaded plunger 254 at the opposite lateral side of the illuminator housing 234. In similar fashion, axial removal of the illuminator 230 from the receiving cavity 217 of the speculum 204 automatically deenergizes the contained light source due to the bias of the laterally disposed switch 248. When assembled by axial insertion into the receiving cavity 217, the lower part of the illuminator housing 234 extends outwardly from the speculum 204. The bottom surface of the illuminator 230 is further provided with a set of electrical charging contacts 244 to enable recharging of the contained batteries, which are dedicated and not removable from the illuminator housing 234. Further details relating to the operation and design of the above assembly 200 are provided in U.S. Pat. No. 8,435,175, incorporated herein by reference in its entirety.

Each of the above described instruments/assemblies can include at least one rechargeable battery as a power source used to energize the contained light source. A set of electrical contacts are provided on the bottom end of either the instrument handle or the portable illuminator to enable charging of the contained batteries using a charging station, requiring proper alignment as well as space allocation for the charging circuitry. Additionally, the inclusion of electrical contacts and other engageable features on the illuminator housing can create a potential source of contamination in regard to patient fluids, as well as impact the overall working life of the illuminator.

Due to the presence of the charging contacts and other features, cleaning of the illuminator of FIGS. 1(a) and 1(b) for reuse thereof is restricted to wiping the housing with a cleaning solution. Since the illuminator is not fluidically sealed, the illuminator cannot be immersed or be similarly handled.

SUMMARY

According to one aspect, there is provided a portable illuminator configured for attachment to a medical device, the illuminator comprising a housing having a disposed light source. A portable rechargeable power supply is connected to the light source, as well as an inductive charging coil, which is disposed within the illuminator housing to enable contactless charging of the contained portable power supply.

In one version and because there are no exposed contacts, the housing of the portable illuminator can be sealed to prevent the ingress of contaminants and thereby significantly improve the effective working life.

The illuminator can include at least one feature that enables releasable attachment to a medical device. According to one embodiment, the medical device is a vaginal speculum that includes an upper blade and a lower blade in spaced relation. In one version, the illuminator can be releasably attached to an inner surface of a blade of the speculum, enabling direct illumination of a target of interest without the need for a light pipe or similar light directing feature.

According to one embodiment, the light source can be automatically energized based on a contained internal switch. For example, the contained switch is at least one of a magnetic reed switch, in which a removable sleeve can cause actuation of the switch. Alternatively, an optical switch, a capacitive switch or other suitable internal switch can be utilized. Alternatively, the light source can be automatically energized based on a contained accelerometer that causes an internal switch to respond to motion of the illuminator.

According to another aspect, there is provided a medical apparatus comprising a medical device. A portable illuminator is releasably attached to the medical device wherein the portable illuminator comprises an illuminator housing, a light source disposed in a distal end of the housing, a portable rechargeable power supply connected to the light source and an inductive charging coil connected to the power supply to permit recharging of the power supply.

The medical apparatus further includes a charging station wherein the portable illuminator can be released from the medical device and engaged, the charging station having a transmitting inductor coil that cooperates with the inductor coil of the illuminator to permit contactless (proximate) charging of the contained battery. In at least one version, the charging station can include at least one feature, such as a receiving slot, which is configured for releasably retaining the illuminator and aligning same with the contained inductor charging coil.

In at least one version, the medical device is a vaginal speculum having an upper blade and a lower blade that cooperate to dilate the vagina of a female patient in order to permit viewing of the cervix. According to at least one embodiment, the illuminator can be releasably attached to the inner blade of the speculum.

The illuminator housing can be sealed to permit cleaning and prevent the ingress of contaminants and can be further configured with an internal switch, such as a magnetic switch, that enables energization of the contained light source based on the presence or absence of a magnet. In one version, a protective sleeve can cover a portion of the illuminator, including the internal switch, the sleeve having a magnet that actuates the internal switch and automatically deenergizes the battery.

Other internal switches, such as a capacitance or an optical switch, can be provided in which proximity can trigger energization of the contained light source. Other alternative features can be provided to automatically energize the illuminator when attached to the upper blade of the speculum. Still further and for unsealed versions of the herein described illuminator, an external switch can also be alternatively provided.

According to yet another aspect, there is provided a method for enabling a medical examination, the method comprising: providing a medical device, and providing a battery-powered illuminator having an inductive charging coil within the illuminator, the inductive charging coil permitting the battery of the contained illuminator to be recharged using a non-contact charging device.

In at least one version, the housing of the illuminator is sealed and includes a contained switch to automatically enable or disable energization of the contained light source. The non-contact charging device can be a charging station having an inductive transmitting coil to cooperate with the charging coil of the illuminator.

In one version, the illuminator can include at least one feature that enables the illuminator to be directly attached to the medical device, such as, for example, an inner surface of the upper blade of a vaginal speculum. This attachment enables direct illumination of an intended target area without need for an intermediate light pipe and simplifies the design/manufacture of the speculum.

One advantage provided is that the herein described illuminator can be made in accordance with an extremely robust and compact design.

Another advantage is that sealing the illuminator housing significantly increases the effective working life of the illuminator, particularly in the presence of patient fluids and other contaminants and in which the entire illuminator can be immersed in a liquid bath for purposes of cleaning. Additionally and due to the sealing of internal components, the illuminator is more resistant to metallic corrosion, electrical patient isolation and static discharges. Moreover and because the illuminator has no intricate pieces, the construction material can be chosen solely based on biocompatibility and chemical resistance to cleaning solutions.

Yet another advantage is that the illuminator is easy to operate and can be charged in a relatively short time (e.g., 1 hour).

Still another advantage in the instance of vaginal specula, is that the illuminator is no longer installed within the receiving cavity of the handle portion. As a result, the design of the speculum can be structurally modified without impacting functionality. For example, the receiving cavity and the light pipe of prior disposable specula are no longer required features, which create significant savings in terms of manufacture and material of the speculum. The herein described illuminator utilizes no moving parts, with the exception of the internal switch, thereby improving its reliability. Additionally and because no moving parts are required, the assembly can be potted (filled with plastic or epoxy), thereby improving its durability and strength.

These and other features and advantages will be readily apparent from the following Detailed Description, which should be read in conjunction with the accompanying drawings.

BRIEF DESCRIPTION OF THE DRAWINGS

FIG. 10 is a functional schematic view of components retained within an exemplary portable illuminator;

DETAILED DESCRIPTION

The following description relates to exemplary embodiments of a portable illuminator or illuminator assembly that is configured for releasable attachment to a medical diagnostic instrument or medical device. More specifically, each of the described embodiments describe attachment and use with a vaginal speculum. It should be readily apparent to those of sufficient skill, however, that the inventive concepts that are described herein are not so restrictive, and therefore can be similarly employed with various other types of medical instruments or medical devices.

In addition, the accompanying drawings are provided in conjunction with this description to depict all of the salient features. To that end, the drawings are not necessarily drawn to scale and therefore should not be relied upon for purposes of dimensions and/or sizing.

Figures 1A, 1B:
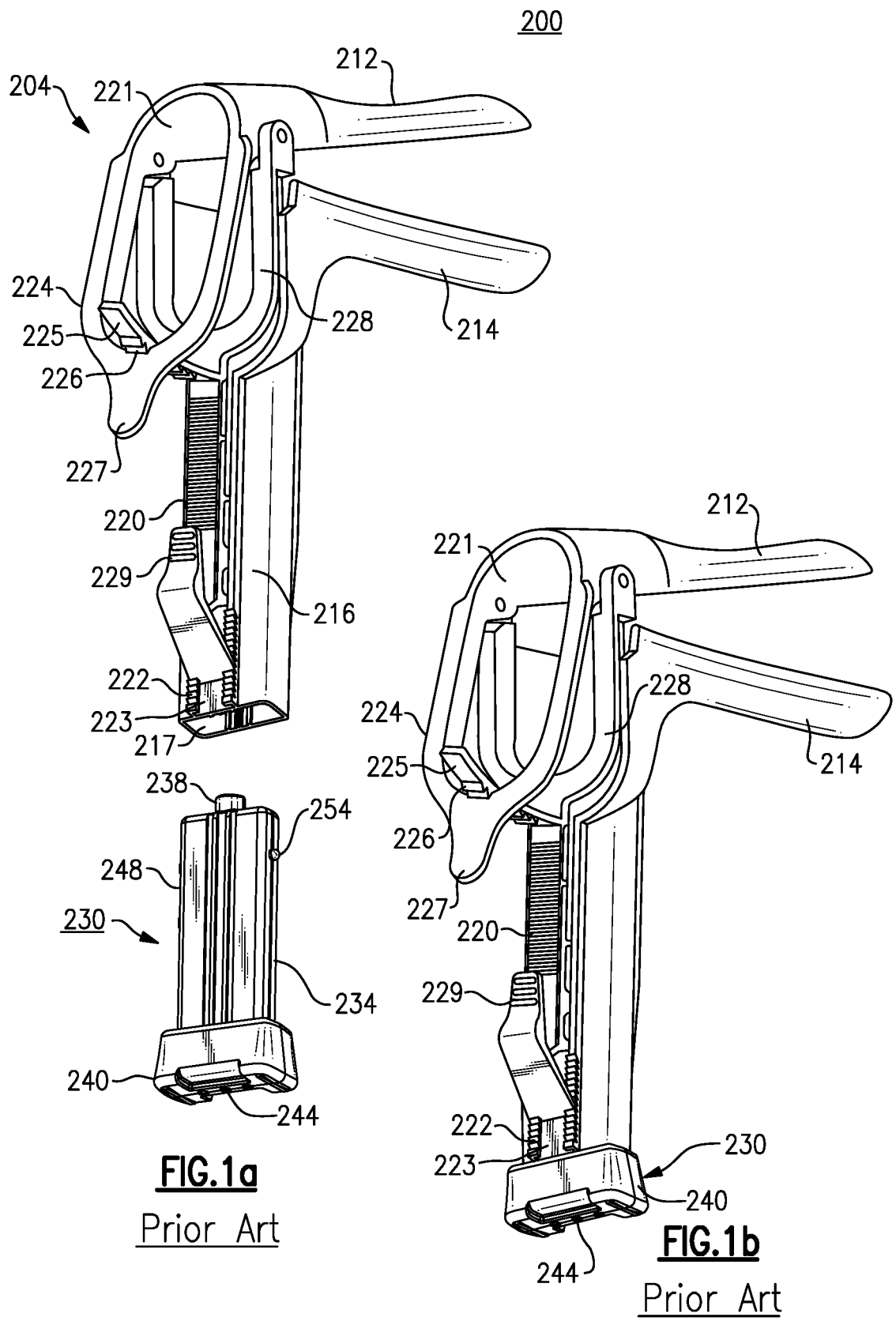
FIGS. 1(a) and 1(b) are rear perspective views of a medical device that is configured to receive a releasably contained illumination assembly in accordance with the known art.
Figure 2:
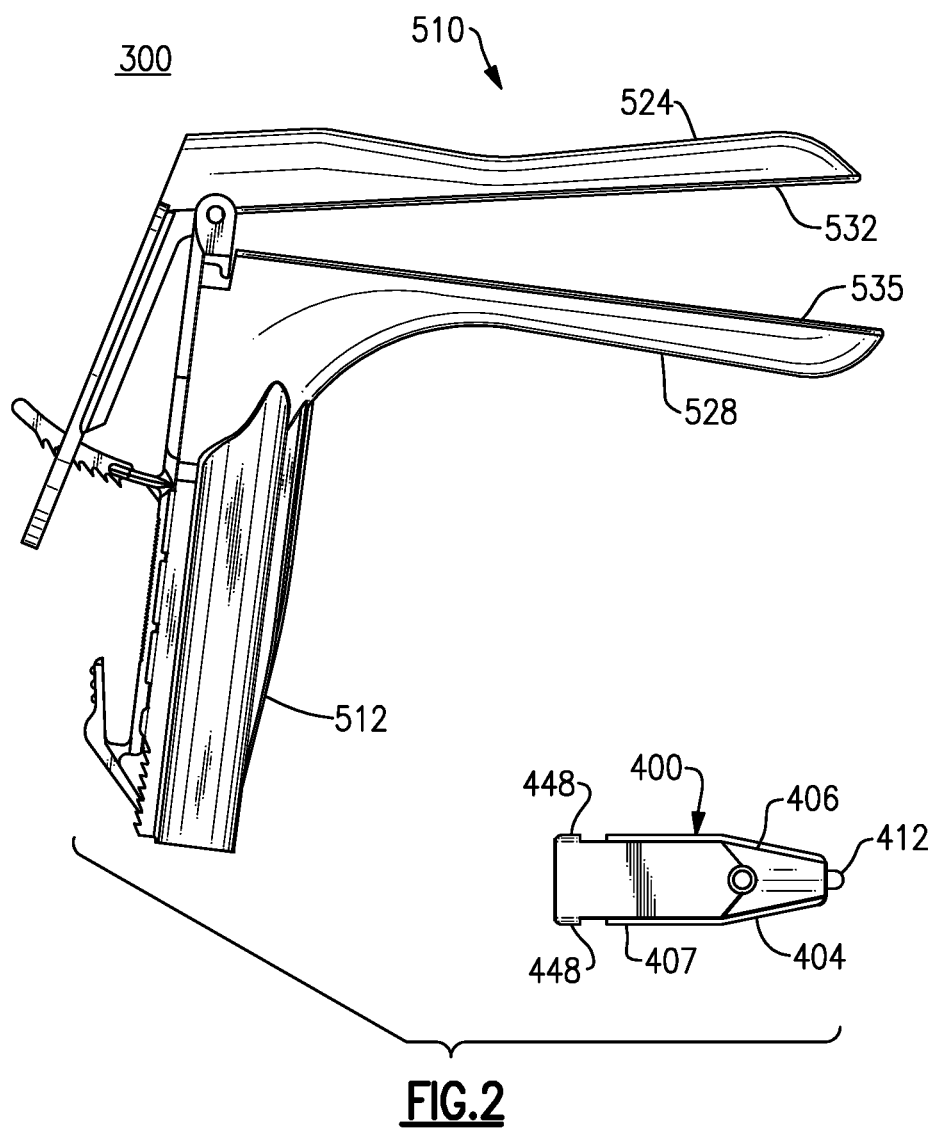
FIG. 2 is a partial assembly view of a medical device having a releasably attachable portable illuminator which is made in accordance with an exemplary embodiment.
Figure 3A:
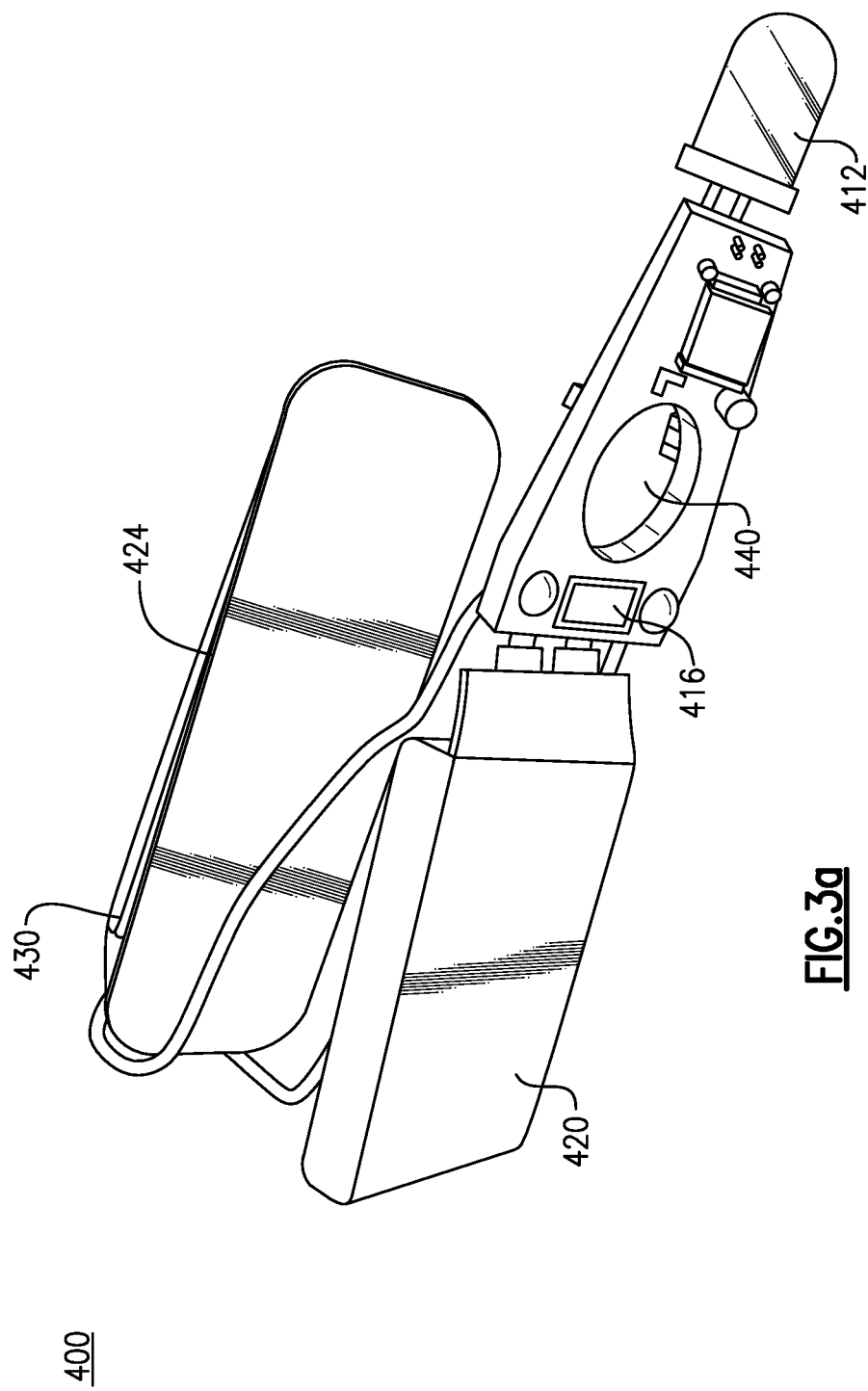
FIGS. 3(a) and 3(b) are partial assembly views taken in perspective of a portable illuminator made in accordance with an exemplary embodiment.
Figure 3B:
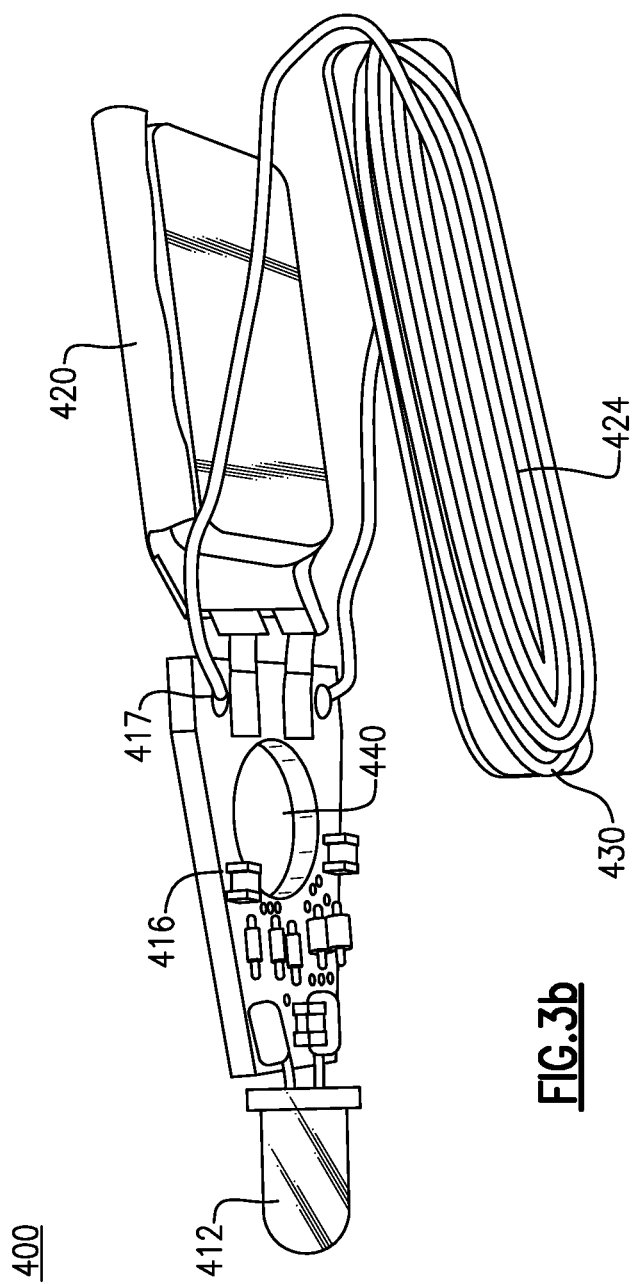
Figure 4A:
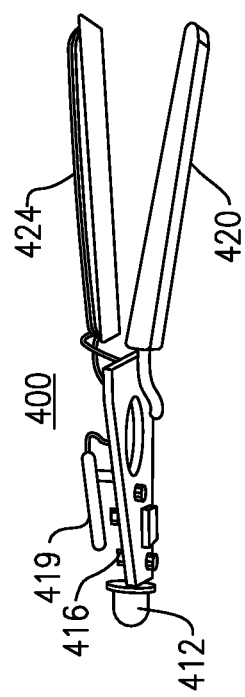
FIGS. 4(a) and 4(b) are side and top views, respectively, of the illuminator of FIGS. 3(a) and 3(b) in a partially assembled condition.
Figure 4B:
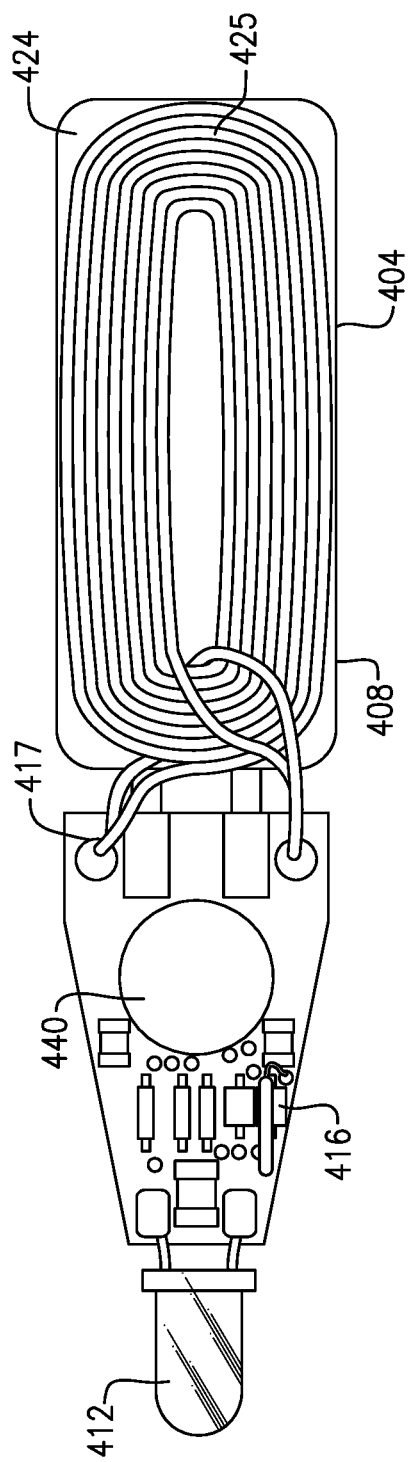

Referring to FIG. 2, a medical instrument assembly 300 is shown that includes a portable illuminator 400 that is configured for releasable attachment to a vaginal speculum 510 and more specifically to an inner surface of an upper blade 524 thereof. Similarly to that shown in FIGS. 1(a) and 1(b), the vaginal speculum 510 is defined by the upper blade 524 and a lower blade 528, each of the blades 524, 528 having a trough-shaped distal portion 532, 535, respectively.

A handle portion 512 depends downwardly from a proximal end of the lower blade 528 that permits the speculum 510 to be hand-held by a user. An articulation mechanism enables the upper and lower blades 524, 528 to be opened in order to dilate the vagina of a female patient and in which the target of interest can be viewed through a rear opening 538 of the speculum 510. In brief, the illuminator 400 is defined by a compact housing 404 having an interior that is sized and configured for receiving a plurality of components.

More specifically and as shown in FIGS. 3(a)-5, these retained components include a light source 412, which is disposed at a distal end of the housing 404, FIG. 2, a circuit board 416, a portable power supply, (i.e., at least one battery 420), and an inductive power charging coil 424. As discussed herein, the components are each retained within the interior of the compact housing 404 of the illuminator 400, which is sealed to prevent the ingress of contaminants and to permit cleaning between uses.

More specifically, the light source 412 can include at least one white LED according to the herein described embodiment, or alternatively a multispectral LED can be substituted, such as an Excelitas multicolor LED. The light source 412 is electrically connected to the circuit board 416, as is the battery 420 and the inductive power coil 424, the circuit board 416 having disposed integrated circuits that enable power from the battery 420 to be transmitted to the light source 412. According to this specific embodiment, each of the inductive power coil 424 and battery 420 are connected to the circuit board 416, such as through soldered contacts 417. According to this specific embodiment, the battery 420 is a 120 mAh Lithium-polymer battery, which when assembled is provided in a proximal portion of the illumination housing 404 in direct relation to the inductive power coil 424, the latter being arranged in an oval wound configuration and having at least one loop 425. According to this specific embodiment, the power coil 424 is defined by a pair of oval-shaped loops 425 disposed in a stacked configuration and disposed within a compartment 430 adjacent the battery 420. Preferably, ferrite backing is used on a surface of the compartment 430 separating the inductive power coil 424 from the battery 420 and also along the walls of the compartment 430 and/or laterally about the battery 420. This backing is provided to improve the inductance of the power coil 424, as well as shield the metals in the contained battery 420 in order to prevent heat that can be generated by resulting electromagnetic eddy currents during a charging operation.

The circuit board 416 according to this specific embodiment and as more clearly shown schematically in FIG. 10, includes an internal switch, such as a sealed magnetic reed switch 419, a wireless Power Consortium Qi-compatible receiver 426, a low-battery detector 428 and a battery charger 432, as well as an LED driver 436, each described in greater detail in a subsequent portion of this description. Use of the established Power Consortium Qi standard enables the herein described illuminator 400 to negotiate power needs in order to wirelessly receive energy sufficient to charge the contained battery 420. Preferably and to avoid regulatory issues with radio emissions, backscatter communication is used, allowing the wireless receiver 426 to observe load changes in the inductive power coil 424 rather than the illuminator 400 and charging station 600, FIG. 8(a), emitting any radio signals. Additionally and according to this exemplary embodiment, the circuit board 416 is defined by a through opening 440 used to retain a plastic sleeve (not shown) and wherein the magnetic reed switch 419 is directly soldered to the circuit board 416.

Figure 5:
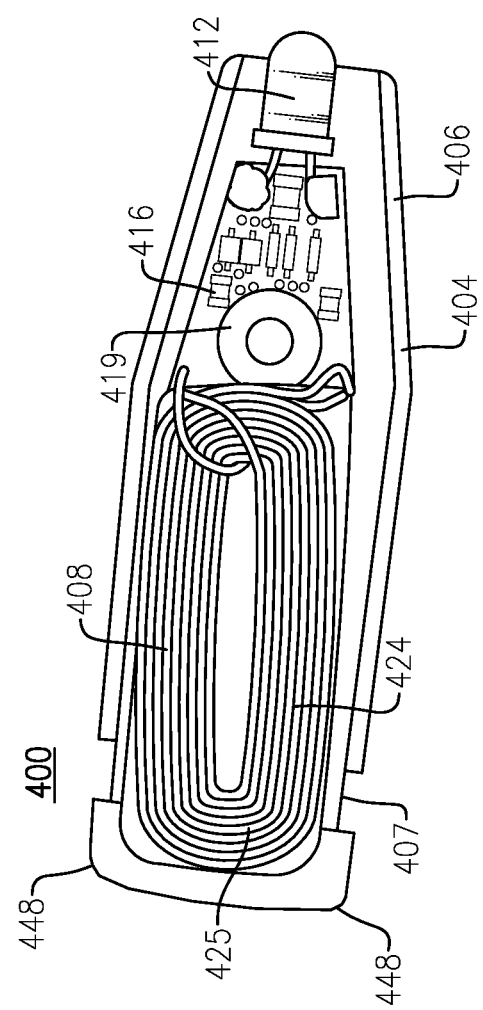
FIG. 5 is a top perspective view of the illuminator of FIGS. 3(a)-4(b) as disposed within a half portion of an illuminator housing.

Referring to FIG. 5, the illuminator housing 404 can be sealed and manufactured, for example, with a pair of separate half sections (only one of the portions being shown in this view) that can be secured to one another using epoxies or by RF or ultrasonic welding wherein the housing 404 can be made from a suitable plastic material, such as a polyamide or polyethylene. In one version, the housing portions can be fabricated using a molding process in which the components can be potted or similarly fixedly retained within the interior 408 of the illuminator housing 404.

Figure 8:
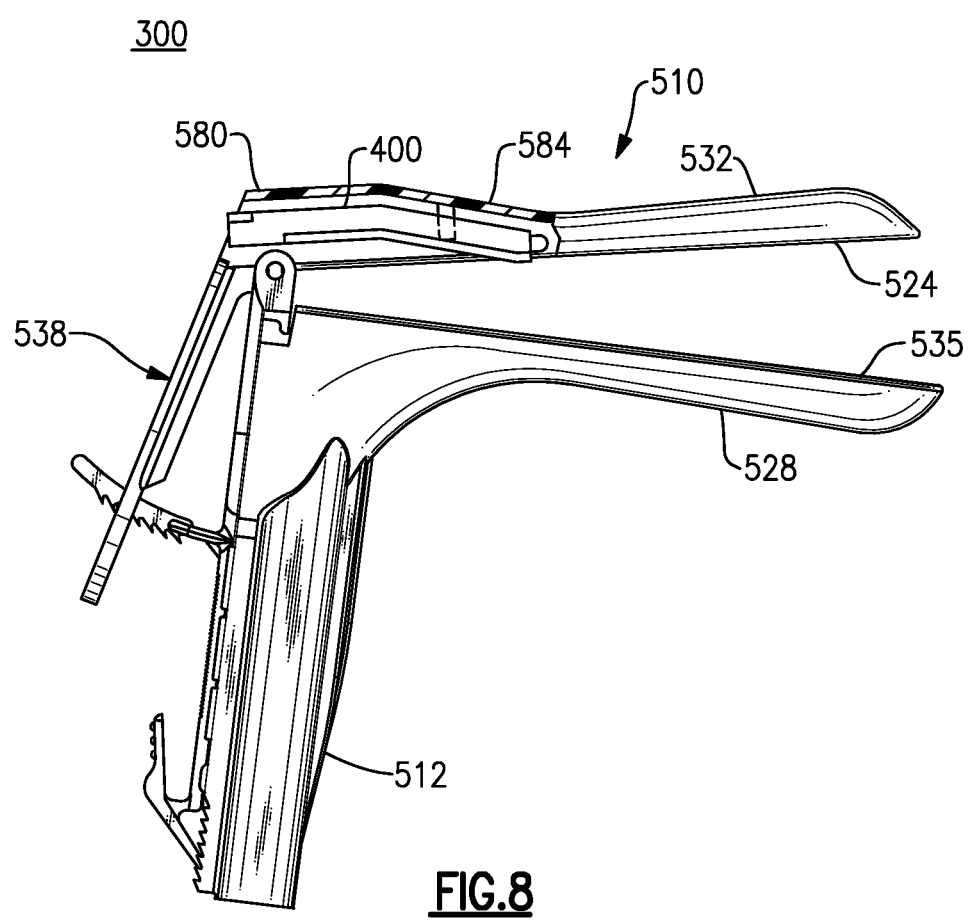
FIG. 8 is a side elevational view of the medical device of FIGS. 6-7(b) having a portable illuminator attached thereto.

Referring to FIGS. 2, 5, 7(a) and 8, the illuminator housing 404 is defined by a distal portion 406 and a proximal portion 407 in which the distal portion 406 is optionally retroflexed relative to the proximal portion 407, for structural reasons in terms of assembly to a vaginal speculum 510, FIG. 8. More specifically and according to this embodiment, the proximal portion 407 is configured with parallel side walls, as well as parallel top and bottom surfaces. The retroflexed distal portion 406 is configured with side walls defined by an inwardly tapering configuration extending to a distal end with corresponding top and bottom surfaces that are angled relative to the top and bottom surfaces of the proximal portion 407. As discussed herein, this particular shaping according to this embodiment is to permit accommodation of the illuminator housing 404 within a similarly shaped interior of an upper blade 524, FIG. 8, of the vaginal speculum 510. The illuminator 400, however, may be positioned along other portions and surfaces of the upper blade 524 and lower blade 528, as desired, such that the light source 412 provides sufficient illumination of an intended target.

When the illuminator 400 is assembled, the light source 412 outwardly extends from the distal end of the housing 404. Alternatively, the light source 412 may be optionally positioned entirely within the housing 404, and capable of providing illumination through a lens, a window, or the like, associated with the housing 404. In this embodiment, the majority of the bottom surface of the illuminator housing 404 is configured with a peripheral edge along the lateral sides of the housing 404 that extends slightly beyond the periphery of the top surface, with the exception of the proximal end. In addition, the top surface of the illuminator housing 404 is provided with a pair or transversely extending tabs 448, FIGS. 2, 9(a), at the proximal end of the illuminator housing 400.

As noted, the light source 412 extends from the distal end of the housing 404 according to this embodiment with the circuit board 416 being disposed in the distal portion 406 of the housing 404 adjacent to and electrically connected to the light source 412. The battery 420 is disposed within a compartment 426 within the proximal portion 407 of the illumination housing 404, with the inductive power coil 424 as disposed in its compartment 430 in a stacked configuration with the battery 420. As herein defined in this embodiment, the battery 420 is adjacent the bottom surface of the illuminator housing 404 and the inductive coil 424 is adjacent the top surface. It is further contemplated that the components within the housing 404 may be arranged in a number of other configurations to facilitate, for example, assembly, heat transfer, sizing, switch activation/deactivation, illuminator performance and circuit design.

According to this exemplary embodiment and according to FIGS. 2 and 6-8, the portable illuminator 400 is configured for releasable attachment to a vaginal speculum 510. As previously noted, the speculum 510 includes an upper blade 524 and a lower blade 528, the latter blade 528 including a handle portion 512 extending downwardly from the lower blade 528 that enables the speculum 510 to be maintained using a single hand of the caregiver. The speculum 510 can be made from an optically clear plastic material, such as acrylic or other suitable materials, with each of the upper and lower blades 524, 528 including the respective trough shaped blade portion 532, 535. The upper and lower blades 524, 528 of the speculum 510 are pivotally attached at their proximal end and define the rear opening 538 that permits viewing of the target (i.e., the cervix of a female patient). The spacing between the distal ends of the upper and lower blades 524, 528 can be adjusted by the user to the pivotal attachment and an articulation mechanism that includes a lever portion extending downwardly from the upper blade 524 and a slide member that upwardly extends from rear side of the handle portion 512, similar to that previously discussed in regard to FIGS. 1(a) and 1(b) in which an arcuate engagement portion extends rearwardly and upwardly from the yoke, including a set of engagement teeth sized to receive a tab at the end of the lever portion. Additional details regarding the operation of this speculum 510 are provided in previously cross referenced U.S. Pat. No. 8,435,175, the entire contents of which are herein incorporated by reference.

Figure 6:
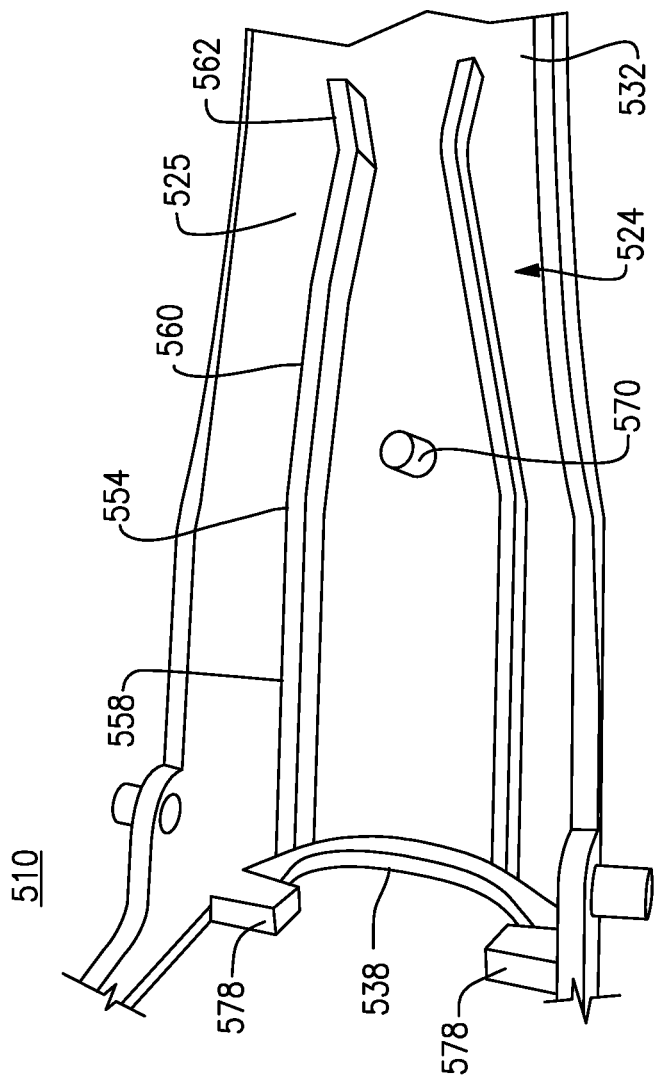
FIG. 6 is a partial perspective view of an upper blade of the medical device of FIG. 2, illustrating exemplary features for releasably retaining the illuminator of FIGS. 2-5.
Figure 7A:
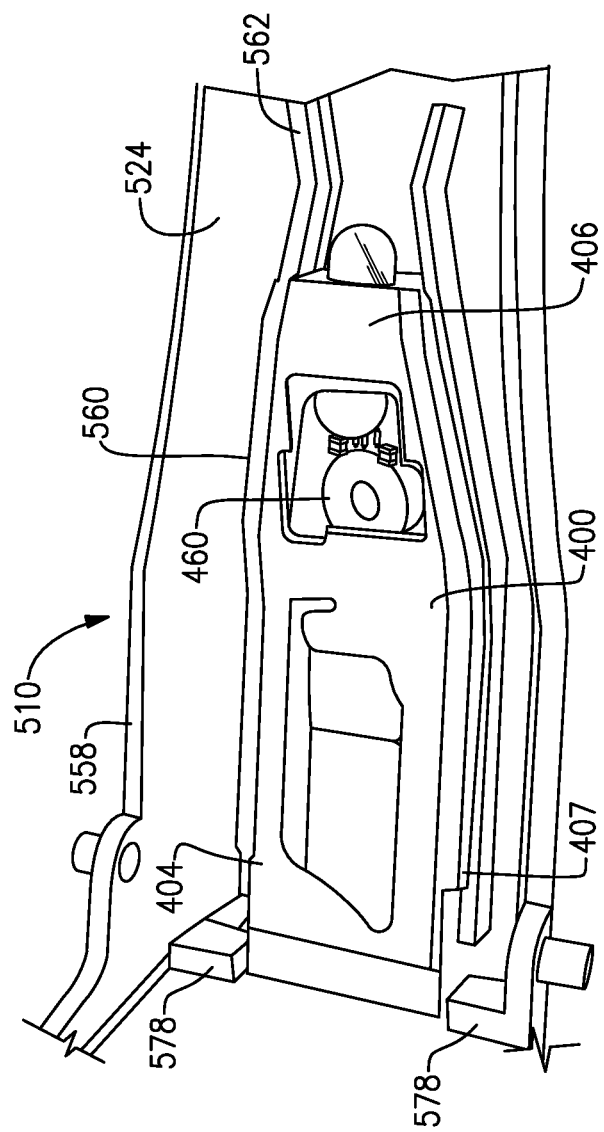
FIG. 7(a) is a partial perspective view, rotated 180 degrees, of the upper blade of the medical device of FIG. 6 having a portable illuminator that is attached thereto.
Figure 7B:
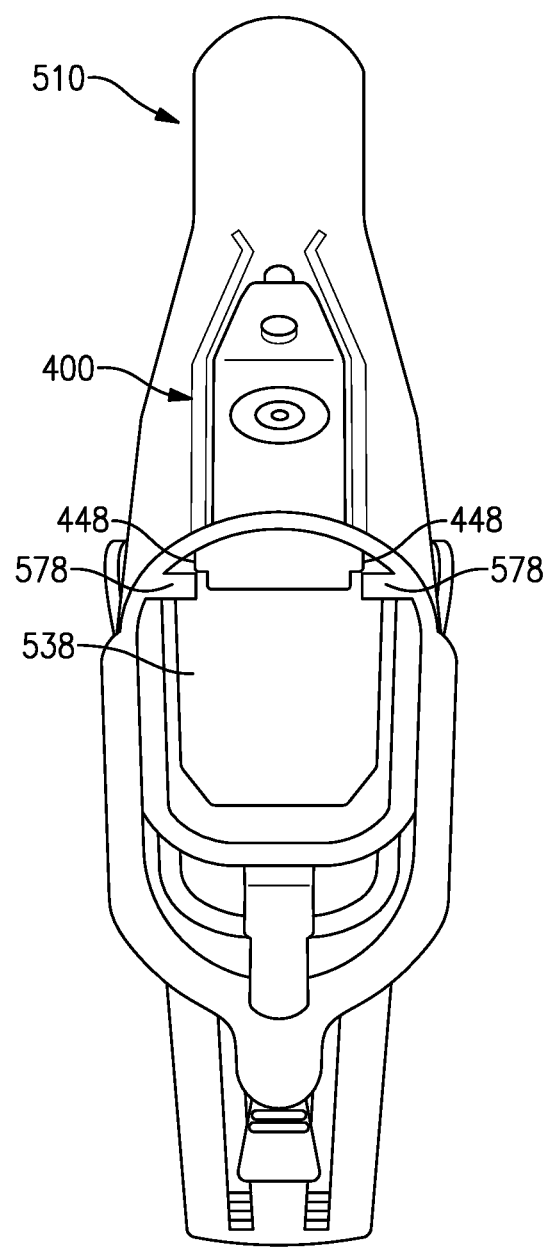
FIG. 7(b) is a partial rear end view of the medical device having the attached portable illuminator of FIG. 7(a)

Referring to FIGS. 6-8, the portable illuminator 400 is releasably attached to the upper blade 524 of the speculum 510. More specifically and according to this exemplary embodiment, the inner surface 525 of the upper blade 524 is provided with a set of mounting rails 554 having a spacing defined therebetween that is sized to essentially match that of the illuminator housing 404 and enabling a press fit. In this specific embodiment, the mounting rails 554 can be formed along with the upper blade 524 using a molding process. Otherwise, the mounting rails 554 can be separately attached or machined. The mounting rails 554 are designed to conform to the sides of the illuminator housing 404 and are defined by a parallel portion 558 adjacent the rear opening 538 of the upper blade 424 that conform to the side walls of the proximal portion 407 with an adjacent portion 560 of the mounting rails 554 that taper inwardly and have a spacing that conforms to the side walls of the distal portion 406 of the illuminator housing 404. A distalmost part 562 of the mounting rails 554 taper outwardly. Moreover and according to this specific embodiment, the proximal end of the upper blade 524 is defined by a raised proximal portion 580 extending to an angled surface 584 that further extends to the trough shaped portion 532. The proximal and distal portions 407, 406 of the illuminator housing 404 are configured to match the profile of the raised proximal portion 580 and the angled surface 584, respectively, when fitted in the interior of the upper blade 524 with the light source 412 being positioned at the outwardly tapered distal part 562 of the mounting rails 554. In this particular version, an optional inner protruding pin or peg 570 extends from the inner surface of the upper blade 524 transversely to the mounting rails 554, the protruding pin 570 being configured for engaging the plastic sleeve that is disposed through an intermediate opening 460 formed in the illuminator housing 404.

According to this version and to install the illuminator 400, the proximal end of the illuminator 400 is first engaged with the proximal rail portion 558 with the top surface of the illuminator housing 404 facing and in contact with the inner surface 525 of the upper blade 524. The illuminator housing 404 is then pivoted to engage the rear tabs 448 within a space formed beneath a set of spaced tabs 578, provided at the proximal end of the upper blade 524 as most clearly shown in FIG. 7(b). The illuminator 400 is then fitted between the conforming mounting rails 554 wherein the illuminator housing and more specifically the contained plastic sleeve (not shown) is engaged with the protruding pin 570.

Figure 12:
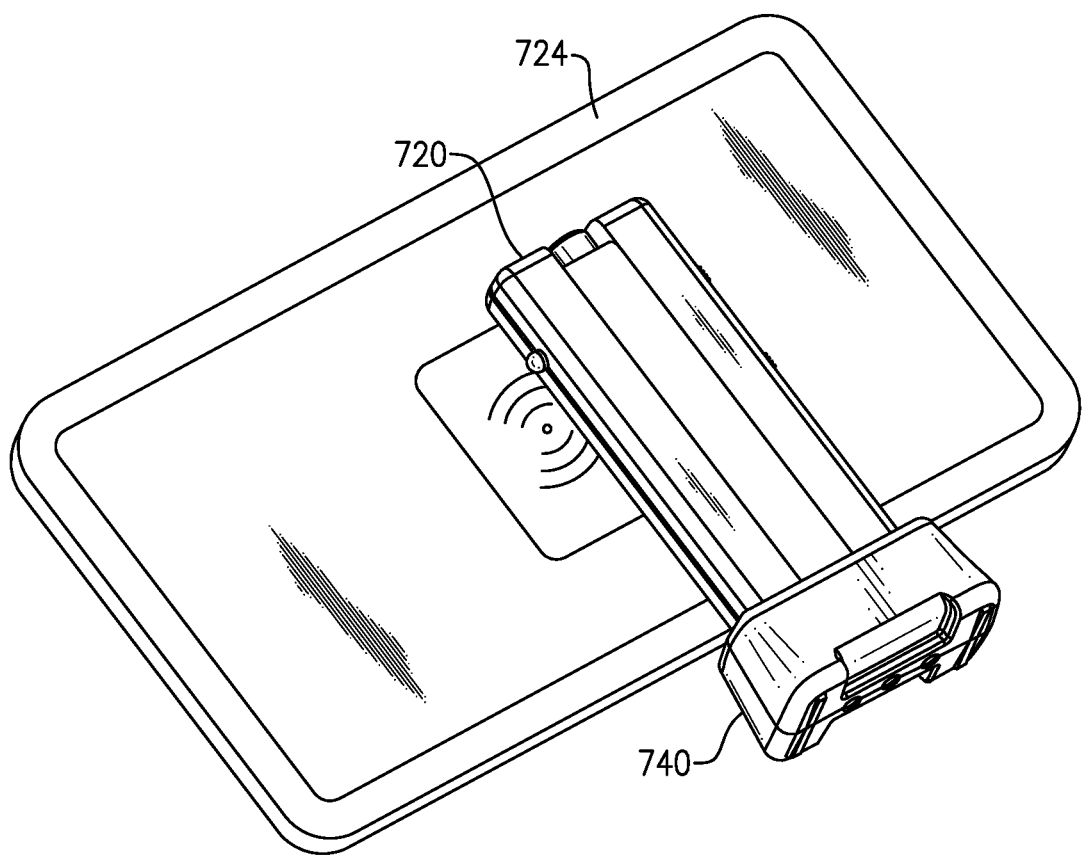
FIG. 12 is a top perspective view of another exemplary illuminator configured for wireless charging of a contained power source.

The configuration including the extending pin 570 is utilized herein as one means to enable attachment to the upper blade 524 of the speculum 510. Alternatively, the mounting rails 554 can be preferably configured as a track to permit a sliding fit of the illuminator housing 404 as advanced and withdrawn from the rear opening 538 of the speculum 510 to permit releasable attachment to the upper blade 524. Other suitable mounting arrangements can also be utilized, provided these arrangements permit releasable and accessible attachment of the illuminator 400 to the speculum 510. In addition and though the upper blade 524 is selected herein for purposes of an attachment surface, the illuminator 400 can alternatively be received by the lower blade 528, whether in the trough shaped portion 535 thereof or in the handle portion 512. One example is depicted in FIG. 12 in which a portable illuminator 720 is defined with a housing 724 having a profile similar to that of the illuminator 230, FIGS. 1(a) and 1(b), wherein an upper end of the illuminator housing 724 can be axially and releasably inserted into a handle portion 216, FIGS. 1(a) and 1(b), and more specifically an enclosed receiving cavity 217, FIGS. 1(a) and 1(b), of a vaginal speculum 204, FIGS. 1(a) and 1(b). When inserted within the receiving cavity 217, the light source retained at the upper end of the illuminator housing 724 is aligned and optically coupled with the proximal end of a contained light pipe (not shown) in the manner described in previously cross-referenced U.S. Pat. No. 8,435,175, the light pipe extending from the handle portion 216 to a distal end adjacent the trough-shaped portion of the lower blade 214 to enable light from the coupled illuminator 720 to be properly directed toward the intended target. In this version and in lieu of charging contacts at the bottom of the housing, the portable illuminator 720 is equipped with a circuit board and battery charging circuit, the latter including an inductive charging coil wherein a contained battery can be charged following direct placement of the illuminator 720 on a planar charging pad 740. Other suitable configurations can be utilized.

In order to remove the illuminator 400 from the upper blade 524 of the speculum 510 in the herein described version, the illuminator housing 404 is first dislodged from the protruding pin 570 by access through the rear opening 538 of the speculum 510. This disengagement causes the illuminator housing 404 to pivot about the supported rear end thereof and allows the rear end and the tabs 448 of the illuminator housing 404 to be slidably removed from the space between the tabs 578 of the upper blade 524 and removed through the rear opening 538 of the speculum 510.

Figure 9A:
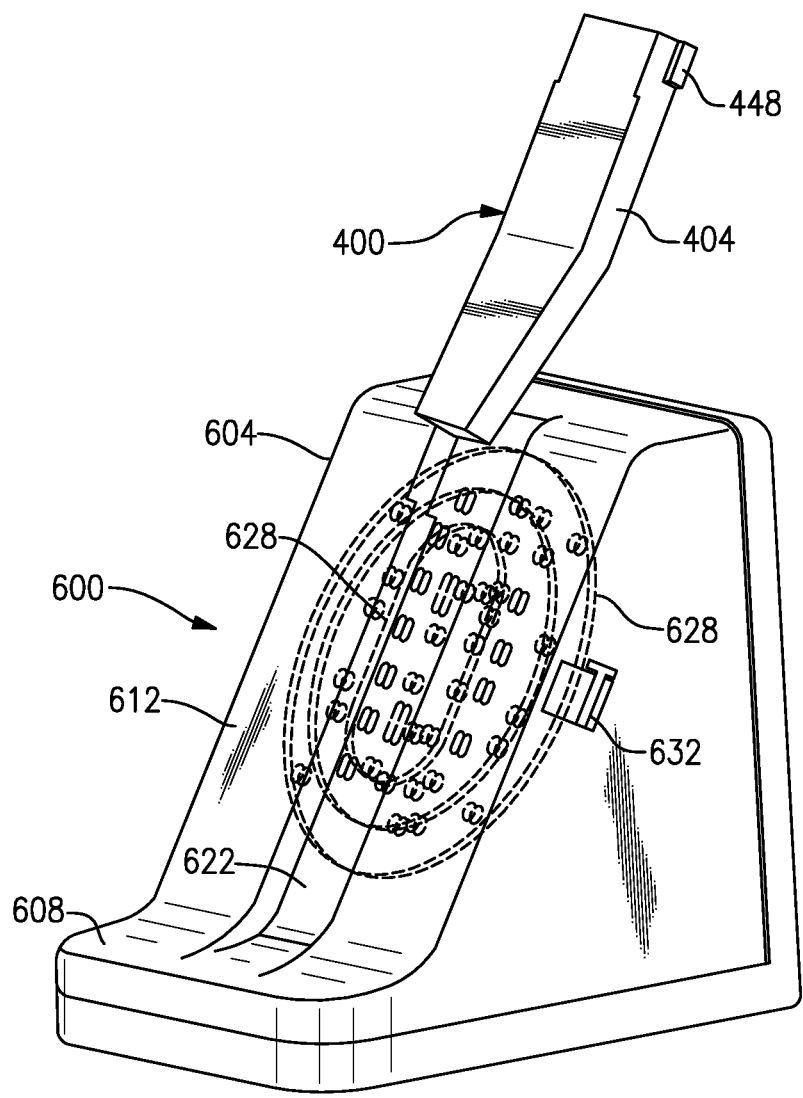
FIG. 9(a) is front perspective view of a charging station made in accordance with an exemplary embodiment that is configured for receiving a portable illuminator.
Figure 9B:
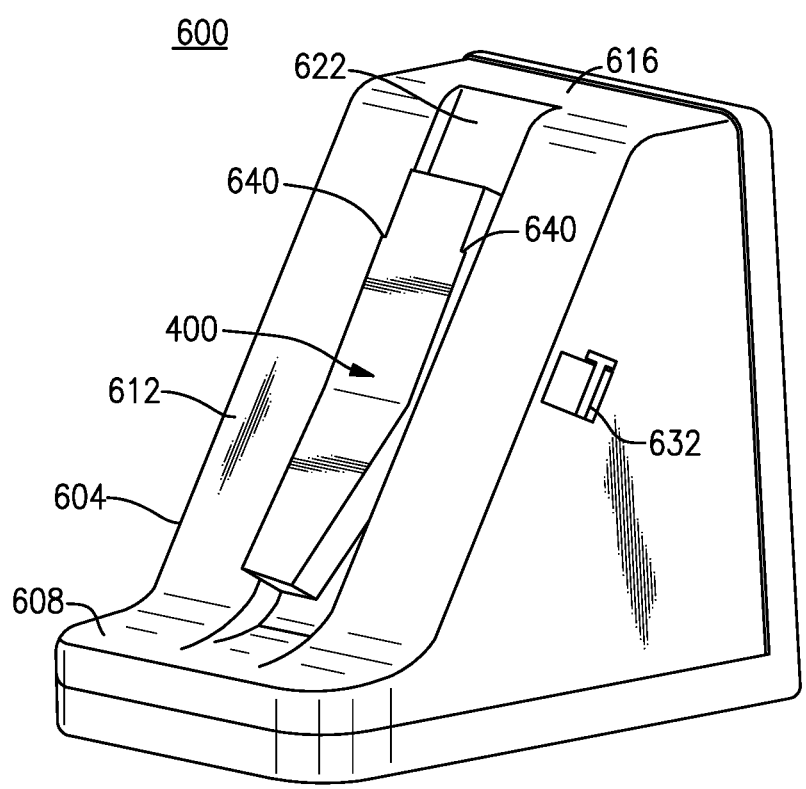
FIG. 9(b) is the front perspective view of the charging station of FIG. 9(a), showing a portable illuminator as installed in a charging position.

As shown in FIGS. 9(a) and 9(b), the illuminator 400 can then be positioned in a charging station 600. According to this exemplary embodiment, the charging station 600 is defined by a housing 604 that enables stable placement on a suitable supporting surface, such as a table, the housing 604 including a planar lower base 608. An angled surface 612 extends upwardly and inwardly from the lower base 608 to a top surface 616. The angled surface 616 is further defined by an elongate receiving slot 622 extending from the top surface 616 of the charging station 600 toward the lower base 608. The receiving slot 622 is sized and configured for retaining and aligning an illuminator 400 for charging thereof, as discussed herein. As shown schematically in FIG. 9(a) and contained within the charging station 600 is an oval-wound transmitting coil 628 (shown in phantom) that resembles the shape of the receiving induction coil 424 of the illuminator 400 to improve magnetic coupling. The power transmitting coil 628 is mounted to suitable circuitry (not shown) including a USB port 632 that is configured to provide power to the station 600, including the power transmitting coil 628. According to this embodiment, a mechanical guide in the form of a shoulder 640 is provided at the top of the elongated receiving slot 622 that enables the illuminator 400 to be inserted in a proper orientation and position within the charging station 600 to enable wireless charging of the illuminator 400.

Still referring to FIGS. 9(a) and 9(b) and according to this embodiment, the illuminator 400 is aligned with the top of the receiving slot 622 with the distal end pointing downwardly and the top surface of the illuminator housing 404 facing the slot 622 wherein the top surface of the illuminator housing 404 is placed in direct contact with the slot 622. The illuminator 400 is then slid downwardly along the receiving slot 622 toward the lower base 608 until the tabs 448 at the proximal end of the illuminator housing 404 engage the shoulder 640, thereby retaining the illuminator 400 and positioning and aligning same in a charging position relative to the contained power transmitting coil 628. The USB port 632 is provided on the exterior of the housing 604 of the charging station 600 to provide electrical power to the contained power transmitting coil 628. Charging of the contained battery 420 is automatically initiated with the ferrite covering protecting the contained battery 420 in spite of the created magnetic field. An LED or other visual or aural indicator (not shown) located on the housing of either the illuminator 400 or the charging station 600 can be connected to the circuitry and configured to be illuminated when charging of the contained illuminator battery 420 has been completed.

Referring to FIG. 10, the operational features of the illuminator 400 are shown schematically in terms of overall functions. In regard to the circuit and according to this exemplary embodiment, energization of the contained light source 412 is controlled by three (3) sources; namely, the magnetic switch 419, the wireless inductive charger 426 and the low-battery detector 428. More specifically, the contained light source 420 is caused to be turned off either: i) when the contained magnetic reed switch 419 is exposed to a magnet, ii) during the charging operation, or iii) when a depleted charge in the battery 420 is determined by the low battery detector 428. An exemplary circuit enabling each of the foregoing functions is shown according to FIG. 11.

As to the first source, a sleeve or cover can be provided (not shown) that includes an embedded magnet (not shown). The sleeve can be sized for placement over the distal portion 406 of the illuminator 400, and more specifically the contained magnetic switch 419. According to this version and upon placement of the sleeve, the contained magnetic switch 419 is caused to close, which produces a short to ground that causes the light source 412 to fade out. Alternatively, the internal switch can be a capacitive, optical or other form of switch that causes energization through actuation of the switch (i.e., opening or closing) based upon proximity of the illuminator 400 with a user (not shown). According to yet another version, the light source 412 can be automatically energized based on a contained accelerometer (not shown) that causes an internal switch to respond to motion of the illuminator 400.

Regarding the second source and while charging proceeds, the LED driver 436 receives a signal from the wireless receiver, that also deenergizes the contained light source 412. Disengagement of the illuminator 400 from the charging station 600 and the power transmitting coil 628 terminates this signal and again causes the contained light source 412 to be automatically energized, according to this embodiment, unless the illuminator 400 has been covered with the protective sleeve or cover (not shown), as previously discussed.

Finally, the depletion of battery power is detected by the low battery detector 428. If the power falls below a specific threshold, a shutdown signal is transmitted to the LED driver 436 that automatically deenergizes the contained light source 420. In each instance, the corresponding shutdown signal relayed to the LED driver 436 cause the contained light source 412 of the illuminator 400 to be deenergized. In addition and when the contained light source is turned off, the battery voltage recovers to a limited degree, which brings the battery voltage above the specific threshold and could cause the light source 412 to cycle on and off. In order to alleviate this technical issue, the detector 428 has hysteresis, which makes the "falling" threshold much lower than the "rising" threshold.

Figure 11:
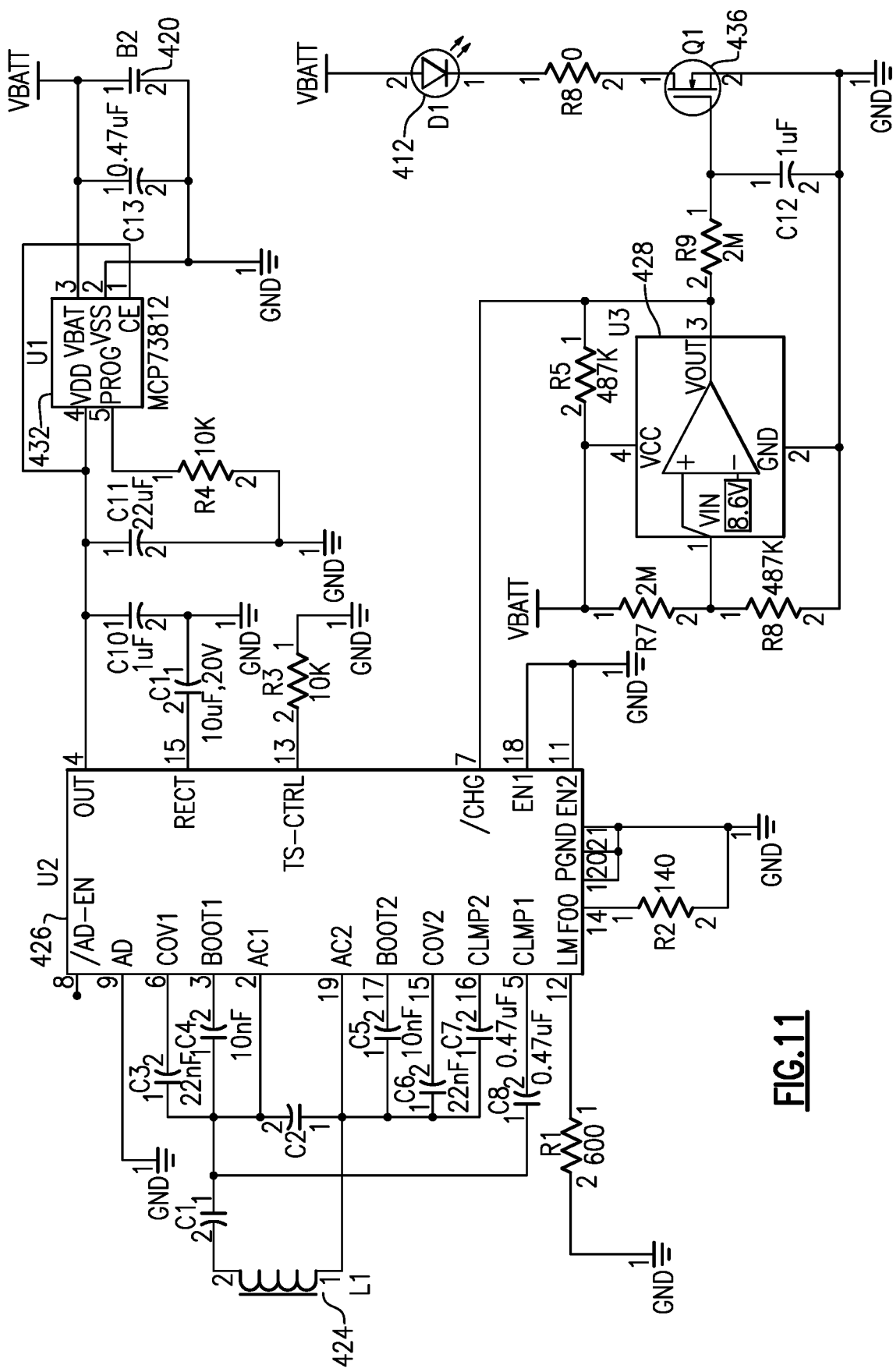
FIG. 11 is an exemplary electrical schematic for a portable illuminator.

As noted, a specific charging circuit is illustrated in FIG. 11 wherein the wireless receiver 426, low battery detector 428 and the magnetic switch 419 are each interconnected with the LED driver 436 to provide the functionality depicted in accordance with FIG. 10. The charging station 600 periodically emits a low-power 126 kHZ signal to detect the presence of a receiving device, such as the illuminator 400, as positioned within the receiving slot of the station. This signal is absorbed by the receiving resonant circuit, which includes the inductive (receiving) coil 424 and is rectified and used by the receiver circuit 426. Storing this energy (C9) and using it for computation, the device responds by encoding a signal (C3, C8) into the impedance of the receiving coil 424. This encoded signal notifies the charging station 600 that an intelligent receiver is present (versus any metal section) and reacts by adjusting the power to the requested amount. This request/adjust pattern regularly repeats for as long as the receiver 424/426 is present. Once the receiver circuit 426 has determined that the power requirements are satisfied and stable, it drives the jCHG output to ground, which causes the LED driver 436 to turn off the light source 412. The receiver 426 also produces a regulated 5V, which is connected to the battery charger 432. The battery charger 432 determines the condition of the contained battery 420 and chooses a charging rate (e.g., 120 mA for healthy, or 12 mA for undercharged). The charger 432 maintains a 120 mA constant current (set by R4) until the battery current reaches a maximum voltage (e.g., 4.2 volts), after which the charger 432 adopts its current output to maintain the maximum voltage until the battery 420 no longer accepts energy.

Still referring to FIG. 11, the circuit for the low battery detector 428 according to this exemplary embodiment includes a fixed resistance 0.6 volt comparator (shown as U3). The battery voltage is divided (R7 and R8) by a fixed ratio and compared to the 0.6 bolts such that when the battery voltage reaches 2.8 volts, the comparator (U3) drives the output to ground, which causes the LED driver 436 to deenergize the light source 412. The LED on/off circuit is a simple field effect transistor (FET, Q1), whose input is on a low-pass filter (R9, C12). Changes to the charge enable/disable line therefore occur on the FET gate very slowly, causing a fade in/out effect any time the state of the enable/disable line changes. This fade is tuned to take about 1 second according to this specific version. The LED current is currently regulated only by a resistor (R6, 12 ohms depending on LED selection). Alternatively, the Q1 may be replaced with a current regulator for power efficiency and stability internally across various battery charges and LED qualities.

PARTS LIST FOR FIGS. 1-12

200 assembly, medical instrument
204 vaginal speculum
212 upper blade
214 lower blade
216 handle portion
217 receiving cavity
220 slide member
221 rear aperture or opening
222 external teeth
223 guide slot
224 lever portion
225 curved portion
226 engagement teeth
227 extending bottom tab
228 yoke
229 lower tongue
230 illuminator, reusable
234 housing, illuminator
238 upper end
240 lower end
244 set of electrical charging contacts
248 external contact switch
254 spring loaded plunger
300 assembly, vaginal speculum
400 illuminator, portable
404 illuminator housing
406 distal portion
407 proximal portion
408 interior, housing
412 light source
416 circuit board
417 soldered contacts
419 magnetic reed switch
420 battery
424 inductive power coil
425 loop, wire
426 wireless receiver
428 low battery charge detector
430 compartment
432 battery charger
436 LED driver
440 opening
448 tabs
460 opening
510 speculum
512 handle portion
524 upper blade
525 inner surface
528 lower blade
532 trough shaped portion
535 trough shaped portion
538 opening, rear
554 mounting rails
558 proximal portion, mounting rails
560 distal portion, mounting rails
562 distalmost portion, mounting rails
570 peg, protruding
578 tabs
580 raised proximal portion, upper blade
584 angled surface, upper blade
600 charging station 604 housing
608 planar lower base
612 angled surface
616 top surface
622 elongate receiving slot
628 transmitting coil
632 USB port
640 shoulder
720 illuminator
724 illuminator housing
740 charging pad It will be readily apparent that numerous modifications and variations are possible within the inventive concepts described herein and in accordance with the following claims.

The invention claimed is:

1. A vaginal speculum comprising:
   an upper blade;
   a lower blade, each of the upper and lower blades including an inner surface; and
   an illuminator comprising:
      an illuminator housing;
      a light source;
      at least one rechargeable battery;
      a charging coil disposed within the illuminator housing and coupled to the at least one rechargeable battery; and
      wherein at least one of the inner surface of the upper blade or the lower blade or the illuminator housing include at least one attachment feature to enable releasable attachment of the illuminator to the inner surface of the upper or lower blade.

2. The speculum as recited in claim 1, in which the inner surface of the upper or lower blade includes a pair of spaced guide rails sized to receive the illuminator housing.

3. The speculum as recited in claim 2, in which the illuminator housing includes at least one tab member sized to engage the pair of spaced guide rails.

4. The speculum as recited in claim 1, in which the inner surface of the upper or lower blade includes a projecting tab that is sized to engage an opening formed in the illuminator housing.

5. The speculum as recited in claim 1, in which the upper and lower blades include a distal end and a proximal end, the speculum further comprising:
   a mechanism for adjusting a spacing between the upper and lower blades in which a viewing aperture is defined in the proximal end of the upper and lower blades.

6. The speculum as recited in claim 5, in which the illuminator is disposed within a raised proximal portion of the upper blade, the illuminator being sized and shaped such that a medical target can be examined through the viewing aperture without interference by the presence of the attached illuminator.

7. The speculum as recited in claim 1, further comprising a handle portion formed at a proximal end of the lower blade.

8. The speculum as recited in claim 1, in which the light source is at least one LED.

9. The speculum as recited in claim 1, in which the charging coil is an inductive charging coil.

10. The speculum as recited in claim 9, further comprising a circuit board disposed distally of the charging coil and the at least one rechargeable battery within the illuminator housing and in which the at least one rechargeable battery and the charging coil are stacked onto one another.

11. The speculum as recited in claim 1, further comprising a switch disposed within the housing.

12. The speculum as recited in claim 11, further comprising a sleeve sized and shaped to fit over the illuminator housing and in which removal of the sleeve from the illuminator housing enables the switch to cause automatic energization of the light source.

13. The speculum as recited in claim 12, in which the sleeve includes at least a portion made from a magnetic material and in which the switch is a magnetic reed switch.

14. A vaginal speculum comprising:
   an upper blade;
   a lower blade, each of the upper and lower blades including an inner surface in which the upper blade includes a raised proximal portion; and
   an illuminator releasably attached to the inner surface of the upper blade within the raised proximal portion, the illuminator comprising:
      an illuminator housing;
      a light source;
      at least one rechargeable battery; and
      a charging coil disposed within the illuminator housing and coupled to the at least one rechargeable battery.

15. The speculum as recited in claim 14, further comprising a moving mechanism for adjusting a relative spacing between the upper blade and lower blade, the upper and lower blades each having a distal trough shaped blade portion and a proximal end defining a viewing aperture, wherein the illuminator is disposed within the raised proximal portion which does not interfere with viewing through the defined viewing aperture.

16. The speculum as recited in claim 14, in which the inner surface of the upper blade includes at least one feature for releasably retaining the illuminator.

17. The speculum as recited in claim 16, in which the at least one feature includes a pair of spaced mounting rails, the illuminator housing being sized to fit between the mounting rails.

18. The speculum as recited in claim 17, in which the light source is disposed at the distal end of the illuminator housing and the charging coil and the at least one rechargeable battery are disposed in stacked relation at a proximal portion of the housing.

19. The speculum as recited in claim 14, further including a switch disposed within the illuminator housing that is configured to enable automatic energization of the light source.

20. The speculum as recited in claim 19, wherein the switch is one of an optical, magnetic, capacitive or acceleration switch.

* * * * *